(12) United States Patent
Lonky

(10) Patent No.: US 6,641,575 B1
(45) Date of Patent: Nov. 4, 2003

(54) SURGICAL VACUUM INSTRUMENT FOR RETRACTING, EXTRACTING, AND MANIPULATING TISSUE

(76) Inventor: Neal M. Lonky, 20776 Juniper Ave., Yorba Linda, CA (US) 92686

( * ) Notice: Subject to any disclaimer, the term of this patent is extended or adjusted under 35 U.S.C. 154(b) by 0 days.

(21) Appl. No.: 09/489,632

(22) Filed: Jan. 24, 2000

Related U.S. Application Data

(60) Provisional application No. 60/117,300, filed on Jan. 26, 1999.

(51) Int. Cl.[7] ............................................. A61M 1/00
(52) U.S. Cl. ................................ 604/540; 600/210
(58) Field of Search ..................... 606/204, 115, 606/123; 604/540, 327, 328; 600/206, 210

(56) References Cited

U.S. PATENT DOCUMENTS

| | | | |
|---|---|---|---|
| 1,294,284 A | | 2/1919 | Logeman |
| 2,082,782 A | | 6/1937 | Allen |
| 3,765,408 A | * | 10/1973 | Kawai .......................... 606/123 |
| 3,768,477 A | | 10/1973 | Anders et al. |
| 4,049,000 A | | 9/1977 | Williams |
| 4,314,560 A | | 2/1982 | Helfgott et al. |
| 4,957,484 A | * | 9/1990 | Murtfeldt ................ 604/102.02 |
| 4,986,839 A | | 1/1991 | Wertz et al. |
| 5,019,086 A | | 5/1991 | Neward |
| 5,123,403 A | | 6/1992 | Lavyne |
| 5,124,364 A | | 6/1992 | Woff et al. |
| 5,196,003 A | * | 3/1993 | Bilweis ................... 128/204.28 |
| 5,224,947 A | * | 7/1993 | Cooper et al. ............... 606/119 |
| 5,250,075 A | | 10/1993 | Badie |
| 5,259,836 A | | 11/1993 | Thurmond et al. |
| 5,281,229 A | * | 1/1994 | Neward ......................... 604/74 |
| 5,395,379 A | | 3/1995 | Deutchman et al. |
| 5,423,830 A | * | 6/1995 | Schneebaum et al. ....... 606/110 |
| 5,472,426 A | | 12/1995 | Bonati et al. |
| 5,472,438 A | | 12/1995 | Schmit et al. |
| 5,507,752 A | | 4/1996 | Elliott |
| 5,693,058 A | * | 12/1997 | Cavanagh et al. ........... 606/119 |
| 5,727,569 A | | 3/1998 | Benetti et al. |
| 5,762,606 A | | 6/1998 | Minnich |
| 5,769,784 A | | 6/1998 | Barnett et al. |
| 5,799,661 A | * | 9/1998 | Boyd et al. .................. 128/898 |
| 5,836,311 A | | 11/1998 | Borst et al. |
| 5,865,730 A | | 2/1999 | Fox et al. |
| 5,865,827 A | | 2/1999 | Bullister |
| 5,885,271 A | | 3/1999 | Hamilton et al. |
| 5,891,017 A | | 4/1999 | Swindle et al. |
| 5,935,136 A | * | 8/1999 | Hulse et al. ................. 606/119 |
| 6,074,399 A | * | 6/2000 | Wallace et al. ............. 606/122 |
| 6,506,166 B1 | | 1/2003 | Hendler et al. |

OTHER PUBLICATIONS

Argenta, L. C. and Morykwas, M. J. (1997) Vacuum–Assisted Closure: A New Method for Wound Control and Treatment: Clinical Experience. Ann. Plast. Surg. 38:563–577.

(List continued on next page.)

Primary Examiner—Eduardo C. Robert
(74) Attorney, Agent, or Firm—Knobbe, Martens, Olson & Bear LLP

(57) ABSTRACT

The invention provides a surgical vacuum device including a vacuum cup sized for attachment to and manipulation of a target tissue. The device further includes a vacuum hose for applying a vacuum to the interior of the cup, and structure for applying a tensioning force to the cup once it has been placed and a vacuum applied. The vacuum device may be utilized with minimal or no trauma to the target tissue or surrounding tissues.

5 Claims, 6 Drawing Sheets

OTHER PUBLICATIONS

Bale, R. J., et al. (1997) Minimally Invasive Head Holder to Improve the Performance of Frameless Stereotactic Surgery. Laryngoscope 107:373–377.

Brock, W. B., et al. (1995) Temporary Closure of Open Abdominal Wounds: The Vacuum Pack. American Surgeon 61:30–35.

Chamberlain, G. and Steer, P. (1999) ABC of labour care: Operative delivery. BMJ 318:1260–1264.

Chua Patel, C. T., et al. (2000) Vacuum–Assisted Wound Closure. AJN 100(12):45–48.

Jukema, G. N., et al. (1997) Vacuum Sealing of Osteomyelitis and Infections of the Soft Tissue. Langenbecks Arch. Chir. Suppl. II (Kongressbericht 1997) 114:581–585.

Kim, E. D. and Lipschultz, L. I. (1997) Advances in the Treatment of Organic Erectile Dysfunction. Hosp. Pract. 32:101–120.

Klemm, B. and Salm, R. (1995) Vacuum–Supported Endoscopic Access. End. Surg 3:58–62.

Morykwas, M. J., et al. (1997) Vacuum–Assisted Closure: A New Method for Wound Control and Treatment: Animal Studies and Basic Foundation. Ann. Plast. Surg. 38:553–562.

Muller, G. (1997) Vacuum–Sealing Technique in Septic Surgery. Langenbecks Arch. Chir. Suppl. Kongressbd 114:537–541.

Mullner, T., et al. (1997) The use of negative pressure to promote the healing of tissue defects: a clinical trial using the vacuum sealing technique. Br. J. Plastic Surg. 50:194–199.

Sames, C. P., et al. (1977) Sealing of wounds with vacuum drainage. Br. Med. J. 2:1223.

Smith, L. A., et al. (1997) Vacuum Pack Technique of Temporary Abdominal Closure: A Four–Year Experience. Am. Surg. 63(12):1102–1108.

Soderdahl, D. W., et al. (1997) The Use of an External Vacuum Device to Augment a Penile Prosthesis. Tech. Urol. 3(2):100–102.

Won, B. et al. (1999) "*Stereotactic Biopsy of Ductal Carcinoma In Situ of the Breast Using an I I–Gauge Vacuum–Assisted Device: Persistent Underestimation of Disease*"; American Journal of Roentgenology, v.173, pp. 227–229.

Pelosi, M.A. et al. (1984) "*Use of the soft silicone obstetric vacuum cup to facilitate delivery and manipulation of large pelvic masses at operation*"; American Journal of Obstetrics and Gynecology; v. 148, pp. 337–339.

* cited by examiner

SURGICAL VACUUM INSTRUMENT FOR RETRACTING, EXTRACTING, AND MANIPULATING TISSUE

This application claims the benefit of provisional application no. 60/117,300, filed Jan. 26, 1999.

FIELD OF THE INVENTION

The present invention relates generally to the field of surgery. More specifically, the present invention relates to a vacuum-type surgical instrument that may be utilized as a retractor, extractor, and manipulator of a target tissue.

BACKGROUND OF THE INVENTION

The quality and efficient progress of a surgical case depends on adequate visualization of the internal organs. A surgeon will typically use retraction devices to move certain organs or hold them in place so that another structure, organ, or pathologic entity can be visualized adequately to facilitate surgery on the structure. The most common devices used for retraction involve metal retractors which have been produced in various shapes and sizes to provide atraumatic manipulation of delicate living tissues. Such sharp or rigid clamp devices, such as forceps, are often coupled to organs and traction applied to move the organ away from the surgical site to expose the surgical area in question. Occasionally the organs are retracted so that adhesions attached to those organs are stretched or placed under tension and can be more easily lysed, cut or dissected. For example, adhesions which connect the fallopian tubes, ovaries and uterus can be better visualized if the uterus is retracted exposing the adhesions so that surgical lysis with a sharp tool or laser dissection can progress more accurately and swiftly.

Complications may result from the use of conventional clamping devices of the prior art. Clamping devices frequently traumatize and damage the tissue or organs to which they are clamped. These complications may be compounded in laparoscopic surgery due to the limited visibility and space constraints commiserate with such surgery.

Laparoscopy involves small incisions (typically on the order of 5 to 12 mm, and up to 20 mm) in the abdomen or pelvis through which instruments or probes are placed for dissection, manipulation, extraction, and other operative techniques. Due in particular to this limited accessibility, there is a need for atraumatic retraction devices that can apply a high degree of leverage and forcefully retract, extract, or manipulate certain intra-cavity structures or organs to facilitate dissection or enhance visualization of adjacent structures.

Suction cups of various shapes and sizes have been used in the field of obstetrics to assist in the vaginal and operative delivery of newborns for over thirty years. Current state of the art involves the suction cup that is applied to the fetal scalp during the second stage (pushing through the birth canal) of labor. The obstetrician applies traction to the infant's head via a "string," "wand" or "flexible or rigid shaft with a handle" coupled to the suction cup. The traction is applied in an outward fashion while the delivering mother pushes, thereby assisting in the delivery of the newborn. These suction cups are typically made of silicone, rubber, vinyl or other plastic, or combinations of plastic and rubber. Suction is generally applied through suction tubing which is coupled to a nipple on the vacuum cup, the nipple communicating with the interior of the cup. The method by which the suction is produced can vary from large stationary mechanical vacuum/suction devices to hand-held pumps similar to that which are used to bleed brake fluid from brake lines of automobiles.

It has been proposed to similarly utilize suction devices to manipulate tissue during surgery. Such proposals have generally fallen short of expectations, and have exhibited various disadvantages. For example, U.S. Patent to Bilweis discloses an endoscopic surgical instrument which includes a tube with a suction cup at one end and a bulb at its opposite end. The cup is placed on a target tissue and the bulb is compressed and released in order to apply a suction to the tissue. The tissue is released by again compressing the bulb. The Bilweis device, however is difficult to utilize in that the surgeon has very little control over the level of vacuum applied to the tissue, and no means by which to determine the level that is applied. Further, releasing the tissue may be difficult or impossible in that the vacuum may not be completely released upon complete compression of the bulb. Moreover, manipulation of the tissue is limited by the direct application of force along the tube, either by movement of the tube or by movement of a trocar through which the tube extends. These fields of movement are not versatile, and may be inadequate for purposes of a given surgery. Additionally, tensioning the Bilweis device requires the assistance of a second medical professional.

SUMMARY OF THE INVENTION

In overcoming these and other disadvantages of the prior art, the invention provides a surgical vacuum device including a vacuum cup sized for attachment to and manipulation of a target tissue. For the purposes of this disclosure, the term target tissue will be used to indicate any tissue to which the device will be applied, and specifically includes organs as well as any other bodily tissue, even if it is not specifically stated. The device further includes a vacuum hose for applying a vacuum to the interior of the cup, and structure for applying a tensioning force to the cup once it has been placed and a vacuum applied. The tensioning structure may be in the form of the vacuum hose itself, a control shaft, a handle, or tensioning cords or hooks coupled to the cup either directly or via the elongated control shaft or handle, but preferably includes a combination of these forms. By so including a combination of manipulation mechanisms, the device provides the surgeon with an added range of motion of the cup, facilitating ease of both placement and application of a tensioning force. The vacuum device may be so utilized with minimal or no trauma to the target tissue or surrounding tissues.

The device may be readily utilized and is particularly desirable in laparoscopic procedures. A trocar is inserted through an incision with a surrounding sheath or cannula. Once the trocar is removed, a compressed cup is advanced through the sheath disposed in the incision. Manipulation of the cup in the abdomen, for example, is facilitated preferably using a combination of the tensioning structures to provide the surgeon with a device that may be utilized in a broad range of procedures.

The invention additionally provides an apparatus by which the tension may be held without the need of a surgical assistant. Once an appropriate traction force is applied to the cup, the tensioning structure, for example, the cord, the hooks, or he vacuum tube are secured in position. The cup may be tethered via the tensioning structure to an external framework such as a frame anchored to or adjacent to the surgical field or directly attached to a self retaining retractor at the incision, or a frame coupled to the table or the like. Alternately, the cup may be tethered to the patient himself via a clamp at the incision site or location.

The device may also be advantageously used to apply a tamponade at a wound site, rupture, laceration, or other bleeding site. By applying a mild vacuum to the site, the target site is squeezed, transmitting a mild pressure which slows or arrests bleeding. This procedure may be utilized both internally, and on external body surfaces as a sort of vacuum tourniquet until the site can be otherwise repaired or treated.

DETAILED DESCRIPTION OF THE PREFERRED EMBODIMENTS

Figure 1:
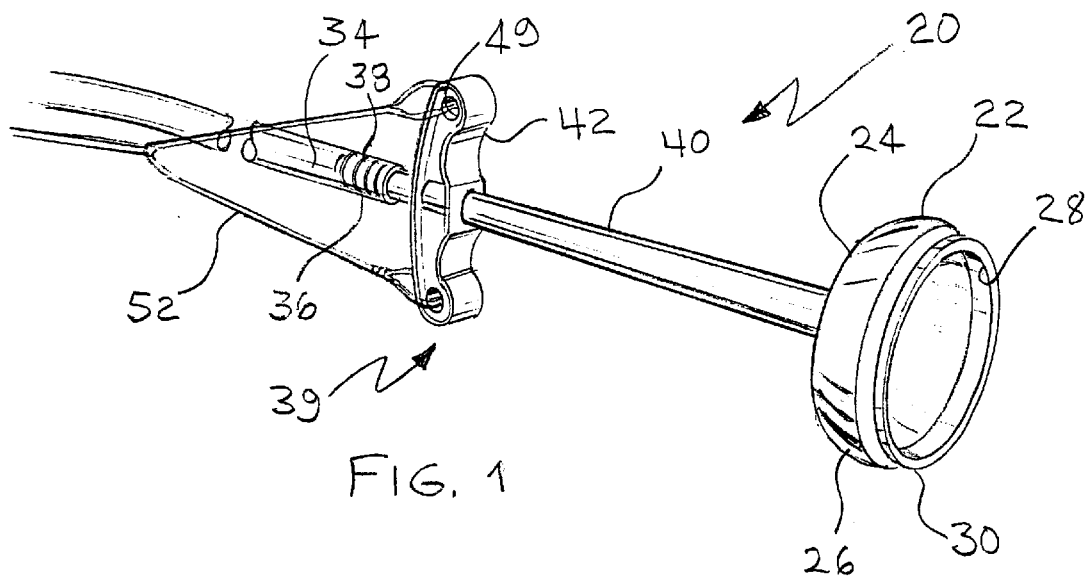
FIG. 1 is a perspective view of the vacuum device constructed in accordance with teachings of the invention and showing a suction cup with attached hose and or wand/handle.
Figure 2:
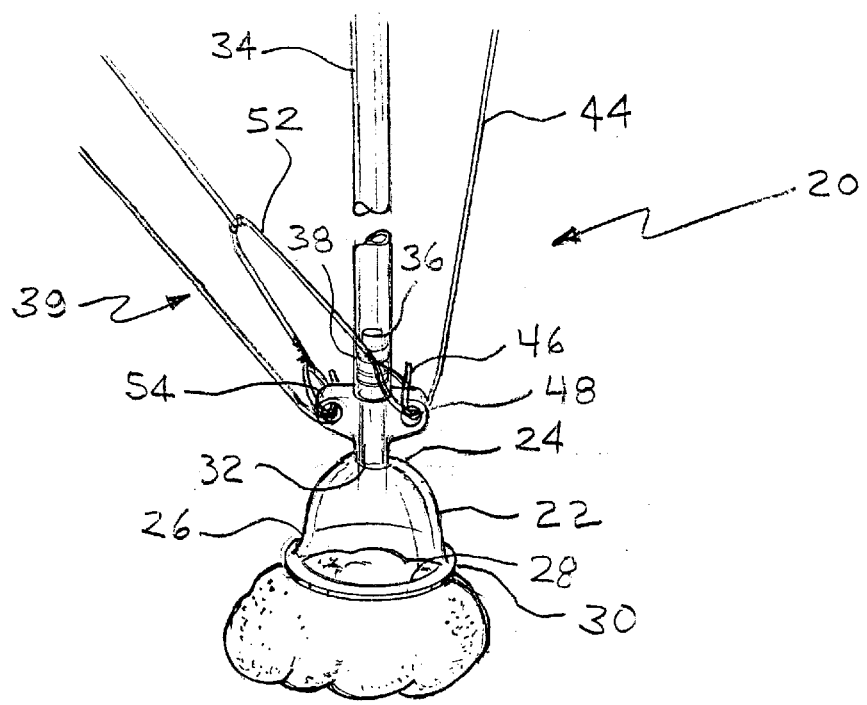
FIG. 2 is a perspective view of an alternate embodiment of the invention wherein guide hooks may be utilized to facilitate placement of the device.

Turning now to the drawings, there is shown in FIGS. 1 and 2 vacuum devices 20 of two different embodiments constructed in accordance with teachings of the invention. The device 20 includes a suction cup 22 having a back wall 24 from which a side wall 26 depends, the side wall 26 forming a basal opening 28 at a side wall edge 30 for placement on an organ, or other tissue. In order to minimize the possibility of damage or trauma to the body tissue, the side wall edge 30 may display a substantially rounded edge. It will be appreciated by those of skill in the art that this rounded edge may likewise facilitate sealing of the cup 22 against tissue, particularly in a mushroom-shaped cup 22 as illustrated in FIG. 1, inasmuch as the rounded edge may readily conform to certain irregularities in the tissue surface and maintain a sealing engagement as the tissue is drawn into the cup 22.

The cup 22 may be of a range of sizes and of various compositions, depending upon the particular application in which it is utilized as described below. The cup 22, however, will preferably run on the order of 3 to 205 mm (approximately 0.1 to 8 inches) in diameter, although it may be smaller or larger. The cup 22 may be of any appropriate shape, so long as a seal may be established with the target tissue, and a vacuum established and maintained at a workable level. The cup 22 illustrated in FIG. 1 has a generally mushroom shape, while the cup 22 illustrated in FIG. 2 has a generally bell shape. The cup 22 may be formed of any appropriate material which is acceptable for surgical usage. For example, the cup 22 may be formed of rubber, plastic, silastic, silicone, plastic such as polyethylene, or metals, such as stainless steel to provide desired cup characteristics for a given usage, e.g., level of flexibility. The currently preferred design utilizes a polyethylene material which results in a relatively transparent cup 22. In this way, the surgeon can readily visualize the interaction of the cup 22 with the tissue (see FIG. 2) and identify potential problems with the engagement or adverse reaction with the tissue.

In order to introduce a vacuum into the cup 22, a vacuum opening 32 is provided in one of the walls 24, 26 of the cup 22. A hose 34 connected to a standard vacuum source (not shown) is coupled to the opening 32 to direct the suction to the interior of the cup 22. The hose 34 is preferably composed of a flexible rubber or plastic, although it may be substantially rigid. While hose 34 may be coupled directly to the opening 32 during molding such that it forms a single piece, or ultrasonically welded or chemically bonded or the like, after molding. A hollow nipple 36 is preferably provided around which the hose 34 may be appropriately secured. Barbs 38 may be provided about the nipple in order to enhance the strength of the coupling. Alternately, or in conjunction with the barbs 38, the hose 34 may be chemically bonded, ultrasonically welded or the like to the cup 22 or nipple 36.

The device 20 also includes tractioning structure 39 by which the cup 22 may be manipulated once placement and vacuum has been achieved. This structure may be in the form of the hose 34 itself, which might function as a tether by which a tractive force may be applied. It will be appreciated that the tractioning structure 39, such as the hose 34, might additionally be of some assistance in manipulation and placement of the cup 22.

In the embodiment illustrated in FIG. 1, the nipple 36 is elongated to form a hollow stem 40, which acts as a control arm by which the cup 22 may be manipulated. In order to further facilitate manipulation of the cup 22 of FIG. 1, a handle 42 is coupled to the hollow stem 40. It will be appreciated that the handle 42 may be separate from the vacuum hose 34.

Further, manipulation of the cup 22 may be provided by an external or removable structure. As shown in FIG. 2, one or more elongated rods 44 having hooks 46 or the like on the distal ends may be provided, as shown in FIG. 2. The hooks 46 may be engaged with openings 48 in the device 20 to maneuver the cup 22 into a desired position on a tissue. Once positioned, the hooks 46 may be removed or used to apply a tractive force to the cup 22. Those of skill in the art will appreciate that, while they may be used on any design, the rods 44 and hooks 46 will be particularly useful in placement and manipulation of cups which do not include a handle or elongated stem, such as the cups disclosed in FIGS. 2 and 3.

Figure 3:
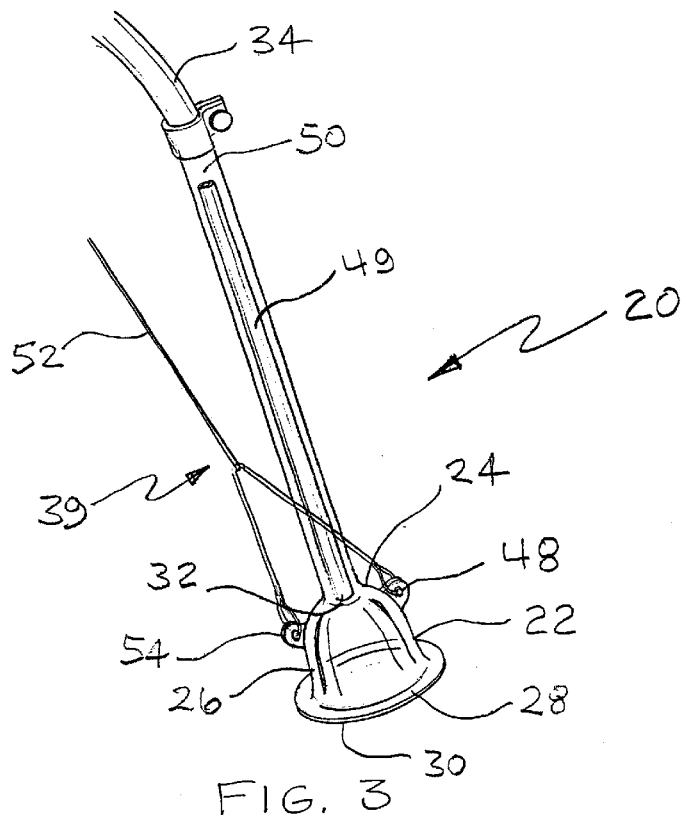
FIG. 3 is a perspective view of a third embodiment of the invention.

As shown in FIG. 3, a device 20 having the flexible hose 34 attached directly to the cup 22, or to only a short nipple 36, or a device 20 having no separate manipulation rod or handle may include an elongated, stiffening rod or stylet 49 which stiffens a segment of the hose 34 and acts as a control arm to permit manipulation of the cup 22. The stylet 49 is preferably hollow, and is disposed within the hose 34 substantially adjacent the cup 22 such that the rod 49 functions in a manner similar to the elongated stem 40 of FIG. 1, while allowing the application of a vacuum. The stylet 49 may further include a tether 50 or the like such that the rod 49 may be removed from the vacuum hose 34 by pulling the rod 49 axially therethrough. Alternately, a rigid sheath may be disposed around the hose 34 and slid in or out as needed.

A tractioning structure which includes a traction cord 52 or the like may be provided. As illustrated in FIG. 1, the traction cord 52 may be coupled to the handle 42 by openings 48 through the handle 42. Alternately, the traction cord may be coupled to the cup 22 by way of ears 54 extending from the nipple 36, as shown in FIG. 2, or directly from the cup 22 as shown in FIG. 3.

Further, an alternate tractioning structure such as the structure disclosed, for example, in the following patents and publications related to obstetrical vacuum extractors may be utilized, the patents and publications being hereby incorporated by reference: U.S. Pat. Nos. 4,512,347; 4,620,544; 4,730,619; 5,395,379; 5,569,265; and 5,713,909; O'Grady et al., *Vacuum Extraction in Modern Obstetric Practice*, pp. 13–21 (The Parthenon Publishing Group, Inc. 1995); Vacca, Handbook of *Vacuum Extraction in Obstetric Practice*, pp. 1–12 (Edward Arnold 1992).

Figure 5:
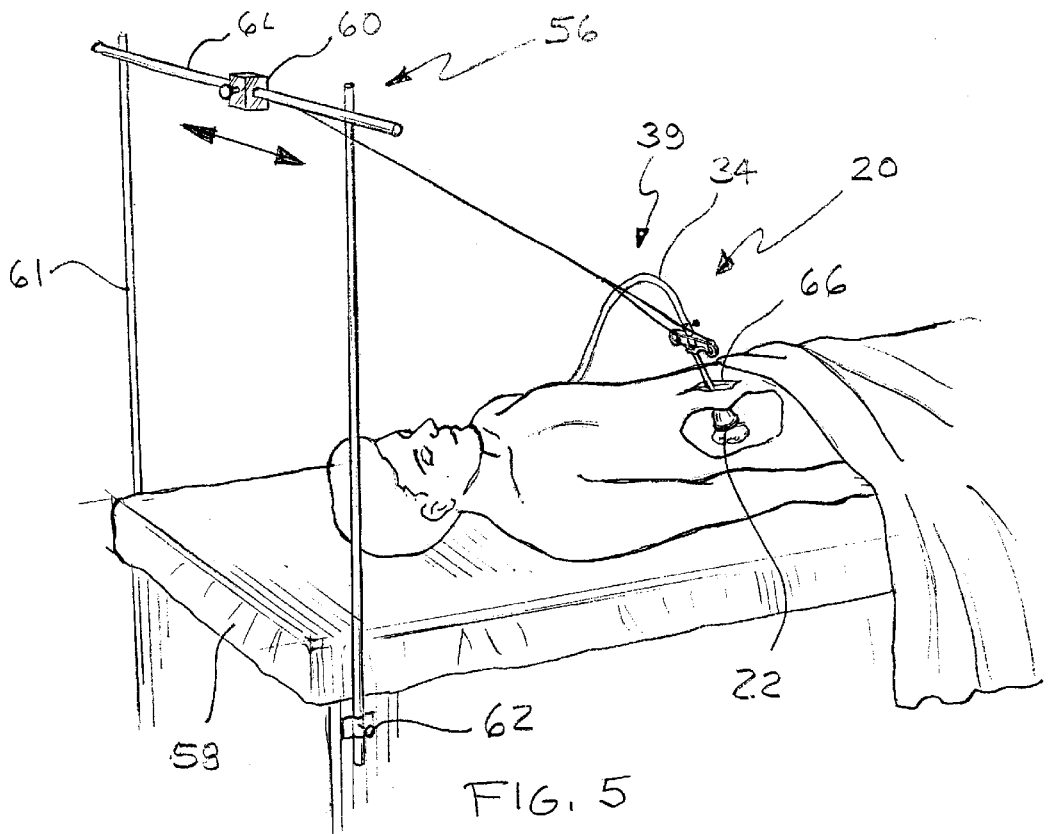
FIG. 5 is a perspective view of a traction arrangement including the device of FIG. 1 wherein the device is coupled to the operating room table to maintain the device in a desired position.

According to another feature of the invention, the traction applied to the cup 22 may be maintained mechanically, in lieu of an assistant or surgeon holding the traction by hand. For example, the cord 52 may be coupled to a frame 56 extending above the operating table 58, as illustrated in FIG. 5. The cord 52 may be clamped to the frame 56 at a sliding bracket 60, the frame 56 preferably comprising-upright supports 61, which are bracketed to the table 58 at bracket 62, and a crossbar 64. The frame 56 is preferably positioned at the head of the table 58, as illustrated in FIG. 5, or at the foot of the table 58 such that it does not interfere with the surgeon's access to the surgical field 66.

Figure 6:
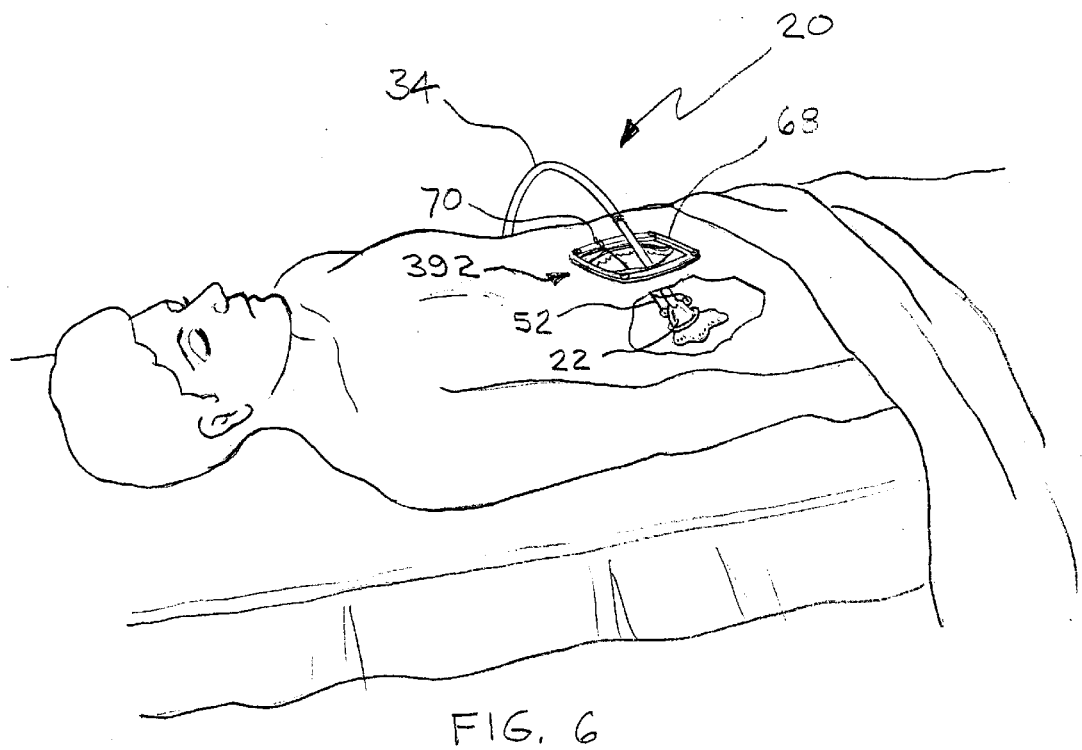
FIG. 6 is a traction arrangement including the device of FIG. 3 wherein the device is coupled to a self-retaining retractor.
Figure 7:
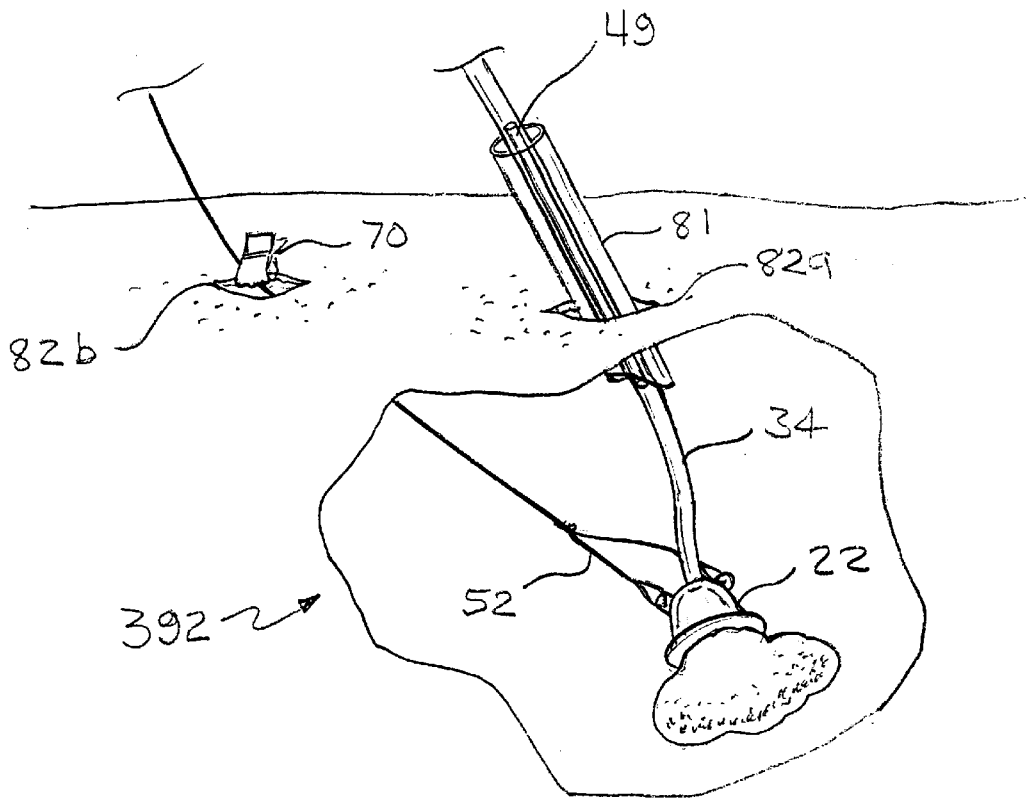
FIG. 7 is a perspective view of the device of FIG. 2 in use during a laparoscopic procedure and wherein the device is tethered by a skin clip.

Alternately, the device 20 may be coupled to a conventional self-retaining retractor 68 as illustrated in FIG. 6. While it may be coupled by any appropriate method, the traction cord 52 may be hooked on a lock nut 70 of the retractor 68. Similarly, during laparoscopic procedures, the cord 52 might be clipped via an appropriate clip 70 directly to the patient's skin, as illustrated in FIG. 7. It will be appreciated that in this particular application, the cord 52 or other tether is applied through one incision, while the suction hose 34 extends through another incision.

Figure 4:
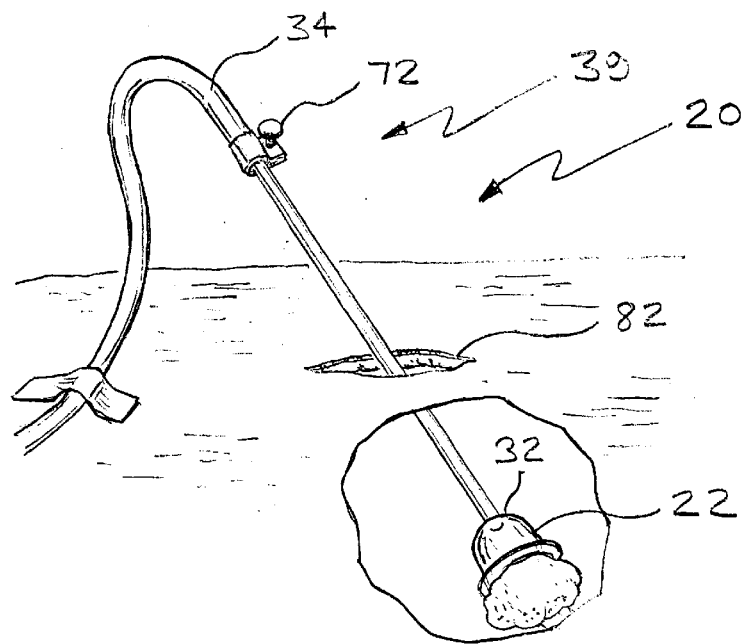
FIG. 4 is a perspective view of a fourth embodiment of the invention.

Additionally, according to one feature of the invention, once the cup 22 is properly placed on the tissue or organ, and the appropriate suction level established, the suction level may be maintained within an acceptable range without continuous adjustment of the pumping device. In order to so maintain the vacuum, a valve or clamp 72 of any known design may be provided between the cup 22 and the pump (not shown). As shown in FIG. 4, the clamp 72 may be disposed such that it simply crimps the flexible vacuum hose 34. In this way, the established vacuum will be essentially maintained on the tissue.

The vacuum device 20 may be utilized in procedures which are intra- or extra-cavitary, that is, procedures which involve body surfaces, orifices, or internal organs, and in both laparotomy and laparoscopic procedures. The device 20 can be utilized as a retractor by attaching to a target organ to allow for better visualization of other organs, as a manipulator to move target organs from one position to another, or as an extractor to "deliver" organs from inside to outside of the body. The level of suction applied to the cup will be dependent not only upon the features of the device 20 including the size of the cup 22, but also on the features of the particular target organ and the type of movement which is required. It will be appreciated that the level of traction force applied will typically be lower than that used when delivering newborns, and, accordingly, vacuum required to prevent release of the cup from the target organ will generally be less than the vacuum level applied with an obstetrical vacuum extractor during delivery.

When a vacuum is applied to a suction cup 22 on a structure having a blood flow, blood will typically pool inside the site, which may lead to the formation of a hematoma. When an obstetrical vacuum extractor is applied to a fetal scalp during vacuum extraction assisted deliveries of newborns, for example, occasionally a small bruise or hematoma occurs on the scalp (cephalohematoma). Additionally, some soft tissue edema and swelling may occur on the area of the scalp where the vacuum was applied. This is called a "chinion" or "caput." Similar results may be possible in tissue to which the invention is applied, but the occurrence and extent of such reactions will be dependent upon the vascularization of the target tissue, the length of time the tissue or organ is held, the material from which the cup 22 is formed, and the level of suction applied. For example, a hematoma may be possible for tissues such as uterine muscle, while it would not be likely in pathologic or physiologic cystic entities, such as ovarian cysts. It will be appreciated, however, that these effects are less likely to result in target tissue during use of the present invention because the level of vacuum applied to such tissue to maintain a traction force is generally considerably less than that required during Vacuum assisted delivery.

Figure 8:
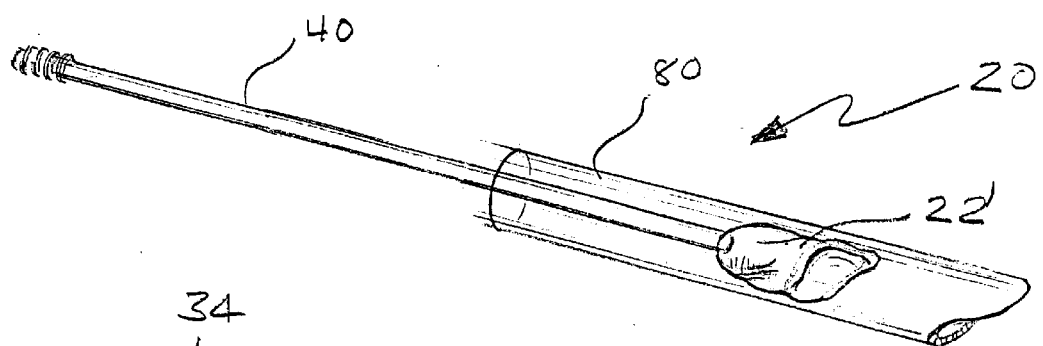
FIGS. 8–13 are perspective views of an alternate embodiment of the device of FIG. 1 for use in a laparoscopic procedure, and views of an exemplary procedure utilizing, the device.
Figure 9:
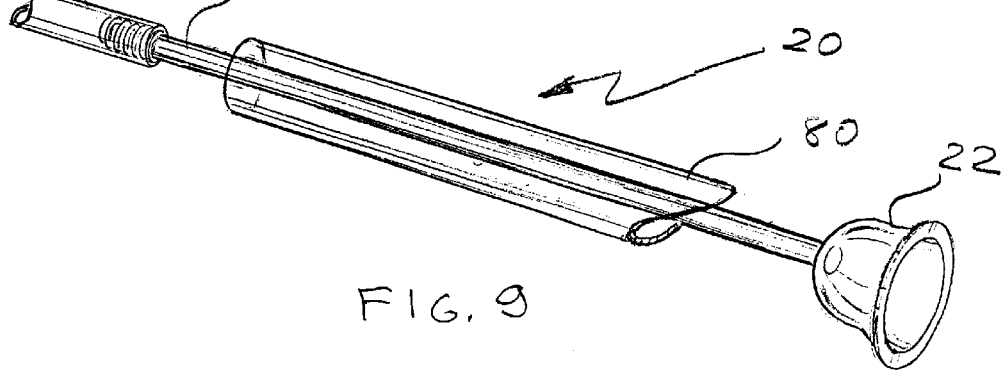
Figure 10:
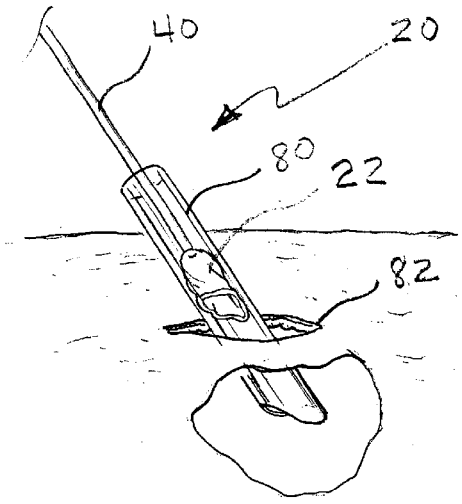
Figure 11:
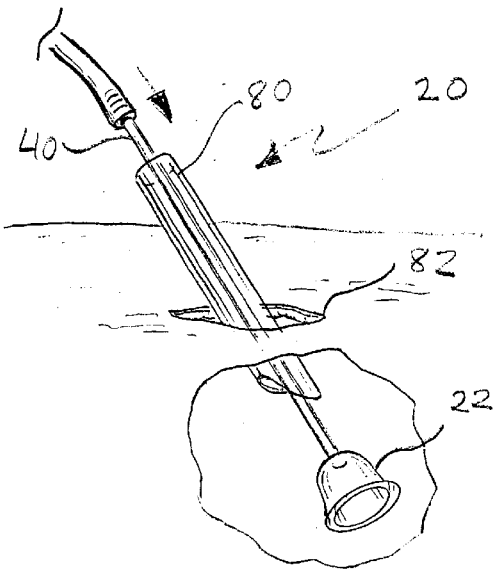
Figure 12:
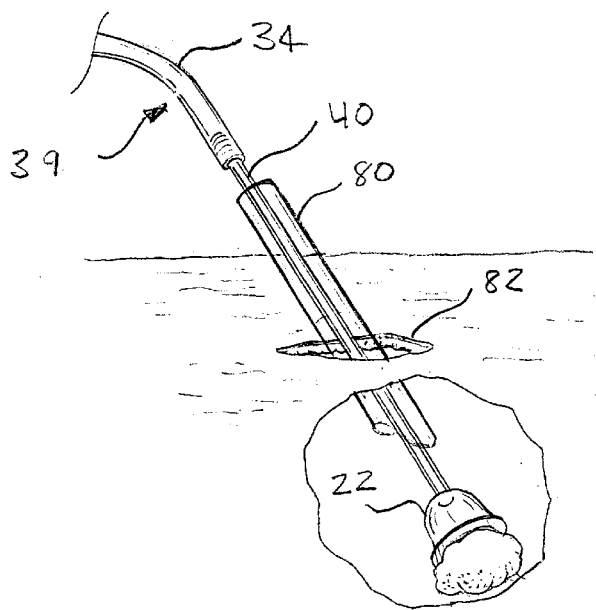

The device 20 is particularly useful during laparoscopic procedures. In order to permit the device 20 to be moved into place through a small incision typical in laparoscopic surgery, the cup 22 is preferably formed of a relatively flexible, but resilient material such that the cup 22 may be advanced through a sheath, cannula, trocar, or other endoscopic device into the body cavity. For example, an incision 82a may be made, a trocar (not shown) and sleeve, cannula, or sheath 80 inserted into the incision 82a, and the trocar removed. The flexible cup 22 for use in laparoscopic procedures is preferably formed of a natural rubber or polymer material such as, for example, silastic, flexible rubber, or a thermoplastic elastomer such as Kraton. Referring to FIGS. 8 and 10, a flexible cup 22 constructed in accordance with teachings of this invention is schematically illustrated folded within a cannula or sheath 80 for delivery through a body cavity through the sheath 80 inserted into the small incision 82a. Once the suction cup 22 is intra-cavitarily positioned, the sheath 80 may be withdrawn slightly from the cup 22 as illustrated in FIGS. 9 and 11.

Figure 13:
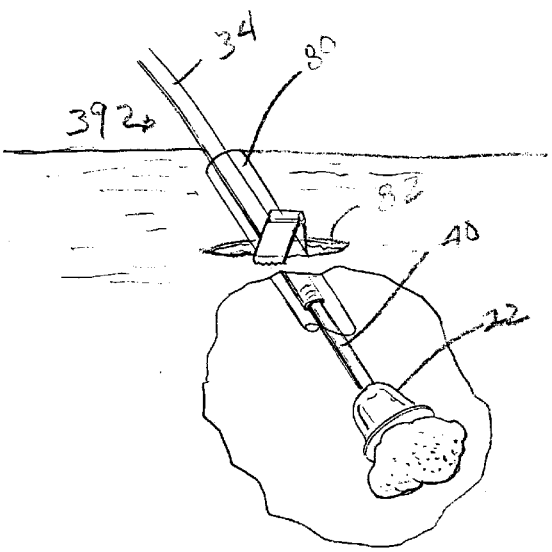

In the embodiment illustrated in FIGS. 8–12, the elongated hollow stem 40 may be used to advance the cup 22 and to position the cup 22. A vacuum may then be applied via the vacuum hose 34, and an appropriate traction applied to the stem 40 or hose 34 to pull the tissue toward the incision 82 site. Under this application of tension, the hose 34 must be securely coupled to the cup 22 and preferably be made of strong flexible rubber or plastic. Using this arrangement, much thought must be given to the location of the incision 82 to provide optimal traction in a desired direction to facilitate surgery. Once traction is applied and a clamp device used on the exterior portion of the hose 34 can both serve to block egress of the vacuum and anchor the hose 34 firmly to the body wall above the incision 82, as shown, for example, in FIG. 13. In this way, the clamp device affixes the hose 34 in the stretched or tension position to the abdominal wall to maintain the retraction. Alternately, a plastic or metal clamp or the like may be used to affix the device 20 to another part of the patient or other structure, such as the table, as illustrated in FIG. 5, for example.

It will be appreciated, however, that the cup 22 may be applied to the target tissue and maneuvered according to any of the arrangements disclosed herein. For example, the cup 22 in FIG. 7, the cup of FIG. 3 is inserted through a trocar 81 extending through a first incision 82a and by means of the stylet 48. If the stylet 48 is then withdrawn to just below the incision line, the hose 34 becomes flexible. The tether 52 or rods 44 with hooks may likewise be delivered through the original trocar or sheath or they may be extended through a second incision 82b, as illustrated in FIG. 2, and utilized to manipulate the cup 22 or apply a tensioning force. In this way, the cup 22 may be tensioned or manipulated at an angle other than would generally be attainable when manipulating the device 20 through a single incision.

By way of example, during a typical surgery for excising an ovarian cyst intact, the cup will be applied to the ovary adjacent or over the cyst area. An incision is then made with a second device through a second sheath to expose the cyst and the surrounding ovarian tissue. The cup is then reapplied directly to the cyst wall. Traction is asserted on the cup and cyst, and counter-dissection performed to free the cyst from the surrounding ovary. Suction is maintained and the cyst is pulled through the original incision or through a second abdominal or transvaginal incision intact. It will be appreciated that the original incision may need slight widening if it is utilized. Similar procedures may be utilized for excising or manipulating tumors in neurosurgical or urological surgeries.

Returning to FIGS. 8–12, when the vacuum is no longer required, the suction may be released by, for example, opening the valve or clamp. The flaccid suction cup 22 may then be reintroduced to the sheath 80, and the sheath removed along with the suction cup 22 from the body by asserting traction on the hose 34, stem 40, or other structure.

It will be appreciated by those of skill in the art that the vacuum device 20 may be utilized in a variety of procedures. For example, occasionally internal organs can become adherent to the abdomen or pelvic sidewalls or to other structures rendering them fixed and immovable. A suction cup appropriately sized for the target organ may be disposed, suction applied, and traction or countertraction applied gently to retract the organ or to lift it out of the body cavity so that adhesions may be lysed by the surgeon or assistant surgeon. Should other tissue obscure visualization of the target organ or adhesions, additional suction devices may be applied.

The suction device 20 is particularly effective in surgery or gynecological surgery involving the extraction or removal of tumors from within organ structures. For example, fibroid tumors (smooth muscle tumors of varying shapes and sizes with rounded smooth surfaces) often are embedded in the wall of the uterus. When the uterine wall is dissected and the tumor exposed, a surgeon's assistant typically uses sharp extraction instruments, such as clamps or hooks, to put traction on the tumor while the surgeon bluntly and sharply dissects the tumor free from the organ. According to the invention, the suction device 20 can be applied to the tumor and traction applied as the surgeon dissects the tumor from the organ. In this way, the surgeon can avoid the additional blood loss that accompanies the use of sharp tools to extract the tumor, as such sharp tools often cause maceration and laceration of the tissues during traction. While the optimal diameter of the cup 22 may vary as it is chosen to correlate with the diameter of the structure to be removed or extracted, it has been determined that a vacuum device 20 including a cup 22 having a diameter on the order of 20 mm up to 80–100 mm and formed of a plastic, metal, silastic, or rubber material is particularly useful in this type of surgery.

By way of further example, if one ovary is attached to a pathologic entity such as a fallopian tube with an ectopic pregnancy and the ovary must remain intact, the suction cup 22 can be applied to the ovary, a vacuum applied, and the adhesions or attachment between the tube and ovary can be better visualized and any attachments more safely lysed. This avoids any sharp instrument being used to manipulate either the tube or ovary, avoiding complications which may lead to bleeding, infection, or unnecessary removal of adjacent normal organs. It has been determined that a vacuum device 20 including a cup 22 having a diameter on the order of 10–50 mm and formed of a flexible plastic, silastic or rubber material is particularly useful in this type of surgery. Similarly formed cups of the following diameters are likewise desirable for the following types of tissues during various procedures: gallbladder, 20–50 mm; uterus 40–100 mm; fibroid 10–100 mm; large ectopic pregnancy, 20–50 mm; cecum (transfixion through laparoscope as assistance in appendectomy), 20–50 mm; tumors, 20–100 mm.

Figure 14A:
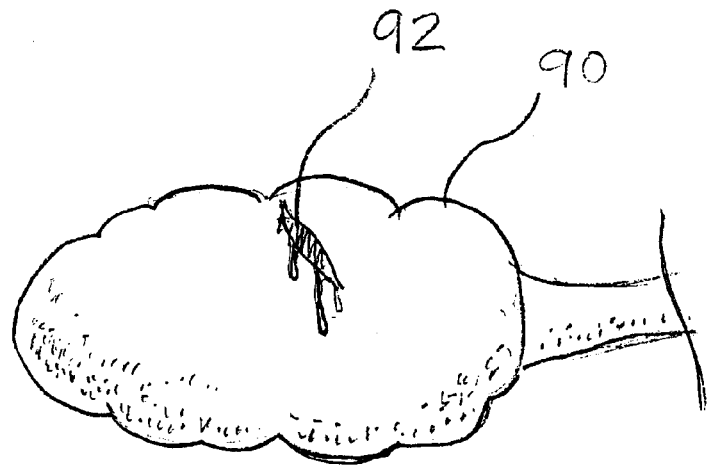
FIGS. 14A and 14B are perspective views of the inventive device applied to laceration site to achieve tamponade.
Figure 14B:
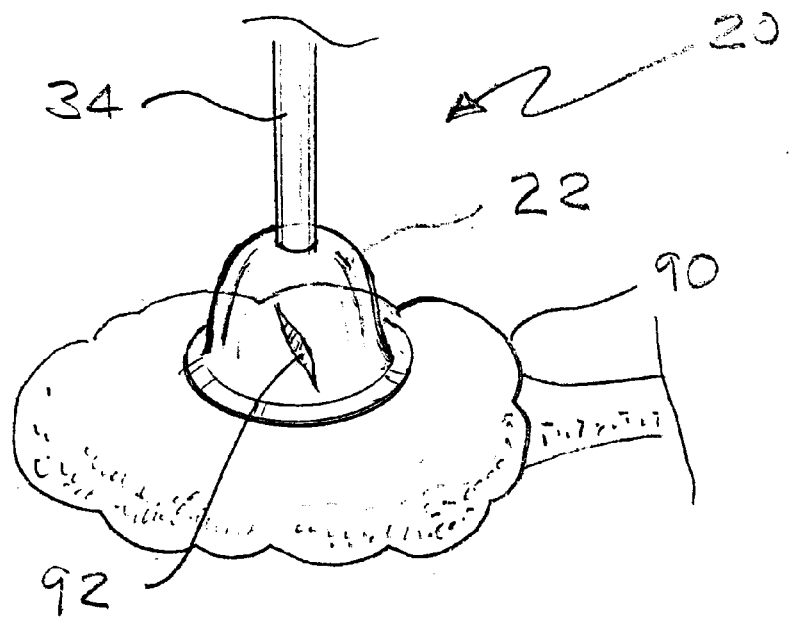

According to another aspect of the invention, the vacuum device 20 may be utilized as a tamponade for bleeding tissue. Thus, if a tissue displays a site which is bleeding, the cup 22 and the vacuum may be applied at that site until the surgery can progress sufficiently to repair or remove the structure in question. For example, if there is a ruptured ovarian cyst or ectopic pregnancy noted during surgery, laparoscopic or otherwise, a suction cup 22 can be applied adjacent or over the bleeding site, and negative pressure applied to curtail bloodflow in and around the bleeding site until the organ or pathologic entity can be safely treated or excised. FIG. 14A schematically illustrates an organ 90 having a ruptured cyst or other laceration 92. Under these circumstances, a cup 22 may be positioned over the laceration site 92 and sufficient vacuum applied to squeeze the tissue surrounding the site and transmit pressure on the periphery of the site, closing the aperture of the laceration to either slow or completely stop the bleeding.

While this aspect of the invention has been described with regard to a bleeding area on an internal tissue, the procedure is likewise applicable to the exterior surface of the body such that the vacuum device 20 acts as vacuum tourniquet of sorts. The cup 22 is applied to a wound and the applied vacuum transmits the tissue deep in the wound site to create a tamponade or pressure effect, much like applying pressure to a bleeding wound. In this way, the procedure is particularly useful on the torso of the body, where a tourniquet could not be applied. The procedure may readily be applied in trauma situations where facilities are unavailable for full treatment of the wound. In an era when blood loss may necessitate transfusion, and transfusion can introduce pathogens such as the AIDS and hepatitis virus to the recipient, any strategy which can efficiently curtail or arrest blood loss as a temporizing method during surgery should be welcomed by the surgical community.

What I claim:

1. A medical retraction device for applying a vacuum from a vacuum source to a target tissue of a patient to facilitate manipulation of the tissue during laparoscopic surgery, said device is capable of extending through an incision in the patient's skin, said device comprising:
   a sheath adapted to be disposed through said incision,
   a substantially flexible vacuum hose for attachment to said vacuum source, a cup having walls defining an internal cavity, said walls including a side wall with a side wall edge forming a cup opening for placement against said target tissue, a vacuum opening extending through one of said walls, said cup being formed of a substantially flexible and resilient material such that it is compressed and disposed entirely within the sheath, said vacuum hose being in communication with said vacuum opening whereby a vacuum is created within said internal cavity to secure the cup to the target tissue, and a substantially rigid rod sized to be attached to the vacuum hose, said rod is also slidable through the sheath and is capable of advancing the compressed cup through said sheath.

2. A method for manipulating a tissue during laparoscopic surgery using the device of claim 1, comprising:

making an incision of sufficient size to insert said sheath into the patient;

inserting said sheath into said incision;

advancing the cup through the sheath disposed in the incision;

releasing the cup from the sheath, thereby decompressing the cup to expose an internal cavity of said cup;

positioning said cup over said tissue;

applying a vacuum to the internal cavity of said cup; and applying traction to said cup to manipulate said tissue.

3. A method according to claim 2, wherein the vaccum is applied from a vacuum source through a flexible vacuum hose.

4. A method according to claim 2, wherein a substantially rigid rod is used to position the cup relative to the sheath.

5. The device of claim 1, further comprising a trochar through which said sheath is inserted.

\* \* \* \* \*